(12) United States Patent
Kamihara et al.

(10) Patent No.: US 12,292,382 B2
(45) Date of Patent: May 6, 2025

(54) CRYSTALLINITY MEASUREMENT DEVICE, RESIN-CONTAINING MATERIAL MANUFACTURING DEVICE, CRYSTALLINITY MEASUREMENT METHOD, AND RESIN-CONTAINING MATERIAL MANUFACTURING METHOD

(71) Applicants: MITSUBISHI HEAVY INDUSTRIES, LTD., Tokyo (JP); AKITA UNIVERSITY, Akita (JP)

(72) Inventors: Nobuyuki Kamihara, Tokyo (JP); Naomoto Ishikawa, Tokyo (JP); Kiyoka Takagi, Tokyo (JP); Sota Kamo, Tokyo (JP); Makoto Yamaguchi, Akita (JP); Mitsutoshi Jikei, Akita (JP); Kazuya Matsumoto, Akita (JP); Mikio Muraoka, Akita (JP)

(73) Assignees: MITSUBISHI HEAVY INDUSTRIES, LTD., Tokyo (JP); AKITA UNIVERSITY, Akita (JP)

( * ) Notice: Subject to any disclaimer, the term of this patent is extended or adjusted under 35 U.S.C. 154(b) by 903 days.

(21) Appl. No.: 17/280,038

(22) PCT Filed: Sep. 20, 2019

(86) PCT No.: PCT/JP2019/037094
§ 371 (c)(1),
(2) Date: Mar. 25, 2021

(87) PCT Pub. No.: WO2020/066940
PCT Pub. Date: Apr. 2, 2020

(65) Prior Publication Data
US 2022/0057331 A1    Feb. 24, 2022

(30) Foreign Application Priority Data
Sep. 28, 2018 (JP) .................. 2018-183782

(51) Int. Cl.
*G01N 21/65* (2006.01)
*B29C 71/00* (2006.01)
(Continued)

(52) U.S. Cl.
CPC ......... *G01N 21/65* (2013.01); *B29C 71/0063* (2013.01); *B29C 71/02* (2013.01);
(Continued)

(58) Field of Classification Search
CPC .. G01N 21/65; G01N 33/442; B29C 71/0063; B29C 71/02; B29K 2101/12; B29K 2995/0041
See application file for complete search history.

(56) References Cited

U.S. PATENT DOCUMENTS

2008/0121891 A1* 5/2008 Lee .................. G01N 21/65
257/E21.53

FOREIGN PATENT DOCUMENTS

| JP | H02502835 A | 9/1990 |
| JP | H0735702 A | 2/1995 |

(Continued)

OTHER PUBLICATIONS

Ramirez et al. "Micro-Raman study of the fatigue fracture and tensile behaviour of polyamide (PA 66) fibres", J. Raman Spectroscopy, 35: 1063-1072, Published online Dec. 10, 2004 (Year: 2004).*
(Continued)

*Primary Examiner* — Tarifur R Chowdhury
*Assistant Examiner* — Akbar H. Rizvi
(74) *Attorney, Agent, or Firm* — HAUPTMAN HAM, LLP

(57) ABSTRACT

A crystallinity measurement device includes a Raman spectroscopy unit configured to acquire a Raman spectrum of resin-containing material including crystalline thermoplastic resin; and an analysis unit configured to calculate crystal-
(Continued)

linity of the crystalline thermoplastic resin based on an intensity of a low-wavenumber spectrum that is a spectrum in a region of less than 600 cm$^{-1}$, in the Raman spectrum.

3 Claims, 5 Drawing Sheets

(51) Int. Cl.
  *B29C 71/02* (2006.01)
  *B29K 101/12* (2006.01)
  *G01N 33/44* (2006.01)

(52) U.S. Cl.
  CPC ........ *G01N 33/442* (2013.01); *B29K 2101/12* (2013.01); *B29K 2995/0041* (2013.01)

(56) References Cited

FOREIGN PATENT DOCUMENTS

| JP | 2015004665 A | 1/2015 | | |
|---|---|---|---|---|
| WO | WO-9927350 A1 | * | 6/1999 | ............. G01N 21/65 |
| WO | WO-2018008562 A1 | * | 1/2018 | ........... B29C 48/022 |

OTHER PUBLICATIONS

English Translation of Kasai et al (WO 2018/008562 A1) Description (Year: 2018).*
Jose Ramirez et al. "Micro-Raman study of the fatigue fracture and tensile behaviour of polyamide (PA 66) fibres", Journal of Raman Spectroscopy, Published online Nov. 12, 2004 in Wiley InterScience (www.interscience.wiley.com); 10pp.
International Search Report and Written Opinon for International Application No. PCT/JP2019/037094 mailed Dec. 24, 2019; 15 pp.
Qin, Deru et al., "Crystallinity Determination of Polylactide by FT-Raman Spectrometry," Applied Spectroscopy, The Society for Applied Spectoroscopy, vol. 52, No. 4, Apr. 1, 1998, pp. 488-495 (8 pp).
Pelletier, M. J., "Raman Spectroscopy Outside the Laboratory", Technical Paper of ISA, Instrument Society of America, vol. 2, No. Part 02, 1998, pp. 69-78 (10 pp).
Jost, Verena et al., "Investigation of the 3-hydroxyvalerate content and degree of crystallinity of P3HB-co-3HV cast films using Raman spectroscopy", Polymer, vol. 133, Nov. 13, 2017, pp. 160-170 (11 pp).
Cherukupalli, Srinivas S. et al., "Online Measurements of Crystallinity Using Raman Spectroscopy During Blown Film Extrusion of a Linear Low-Density Polyethylene", Polymer Engineering and Science, vol. 44, No. 8, Aug. 1, 2004, pp. 1484-1490 (7 pp).
EESR for EP Application No. 19864020.3 dated Jul. 26, 2021 (10 pp).

* cited by examiner

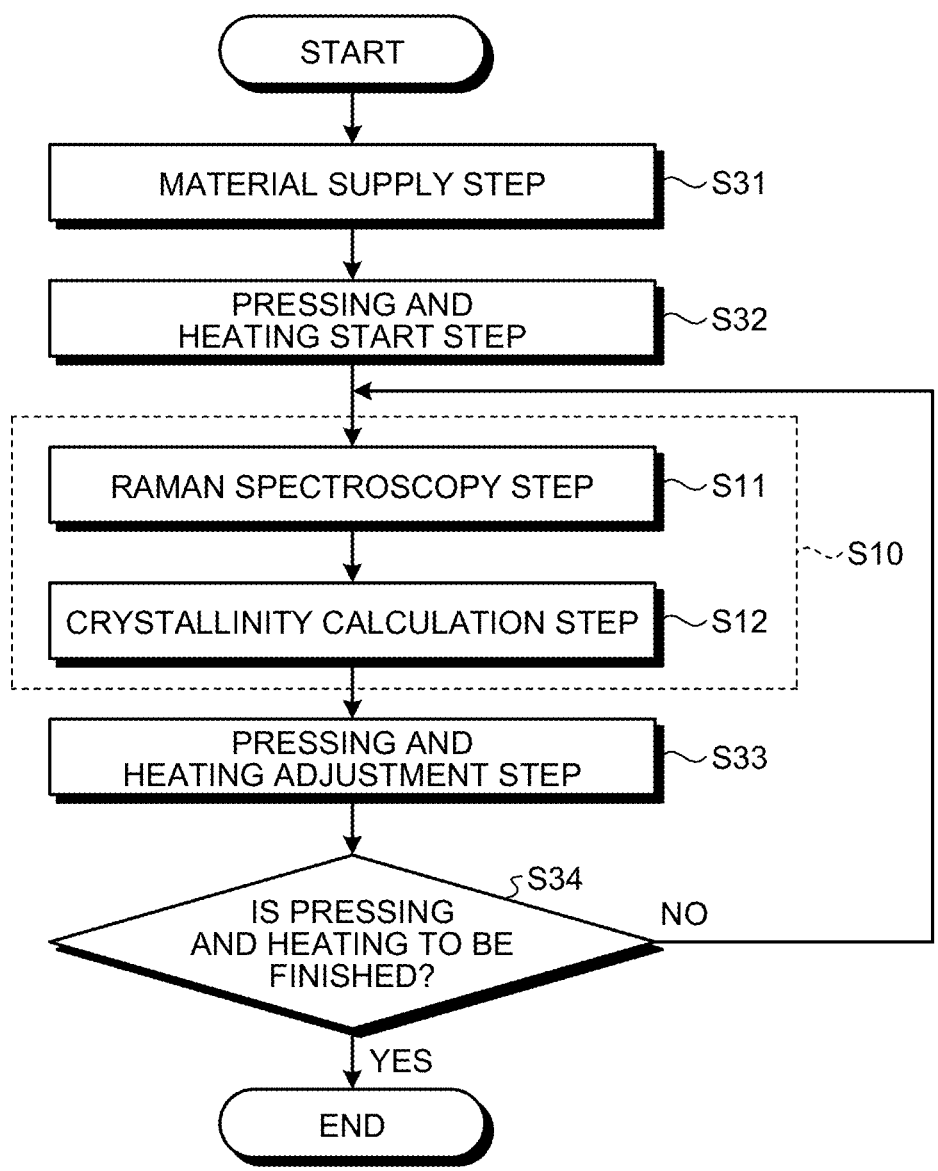

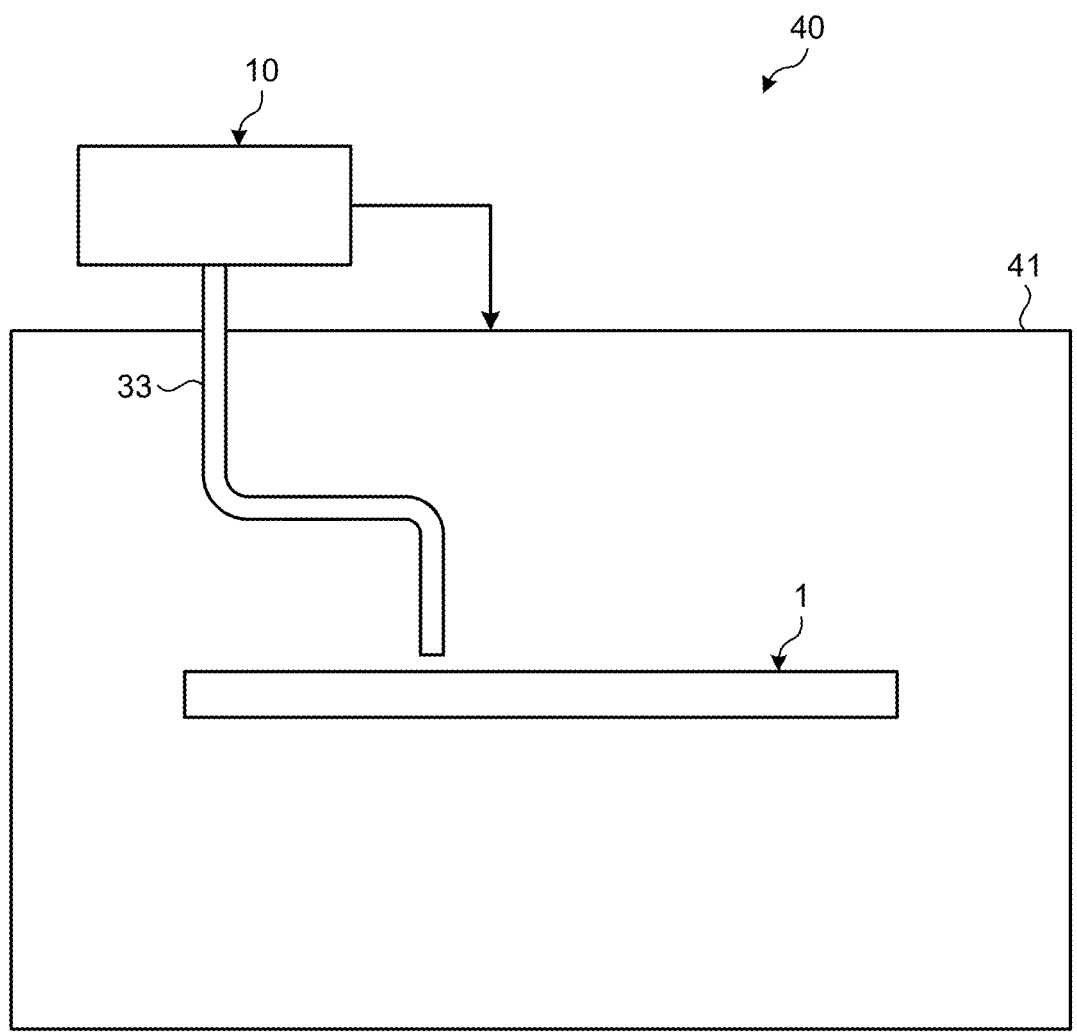

CRYSTALLINITY MEASUREMENT DEVICE, RESIN-CONTAINING MATERIAL MANUFACTURING DEVICE, CRYSTALLINITY MEASUREMENT METHOD, AND RESIN-CONTAINING MATERIAL MANUFACTURING METHOD

RELATED APPLICATIONS

The present application is a National Phase of International Application Number PCT/JP2019/037094 filed Sep. 20, 2019 and claims priority to Japanese Application Number 2018-183782 filed Sep. 28, 2018.

FIELD

The present invention relates to a crystallinity measurement device, a resin-containing material manufacturing device, a crystallinity measurement method, and a resin-containing material manufacturing method.

BACKGROUND

It is known that the crystallinity of crystalline thermoplastic resin changes depending on its molding conditions, and the quality of resin-containing material changes accordingly. As a method for measuring the crystallinity of crystalline thermoplastic resin, a method in which a Fourier transform infrared spectrometer is used to measure an infrared absorption spectrum of crystalline thermoplastic resin by a transmission method and the crystallinity of a thick site of the crystalline thermoplastic resin is calculated based on measurement values of the infrared absorption spectra in which the wavenumber region is from 4,500 cm$^{-1}$ to 2,000 cm$^{-1}$ in the infrared absorption spectra-is known (see Patent Literature 1).

CITATION LIST

Patent Literature

Patent Literature 1: Japanese Patent Application Laid-open No. 2015-004665

SUMMARY

Technical Problem

In the method in Patent Literature 1, the crystallinity of a thick site of crystalline thermoplastic resin is calculated by using a reference sample in which the thickness and the crystallinity, which are factors affecting the shape of infrared absorption spectra in a high wavenumber region with a wavenumber region of 4,500 cm$^{-1}$ to 2,000 cm$^{-1}$ among wavenumber regions of 650 cm$^{-1}$ to 4,000 cm$^{-1}$ generally used for molecular analysis, are accurately controlled. Thus, for example, the method in Patent Literature 1 has a problem in that when materials other than crystalline thermoplastic resin, such as thermosetting resin, thermoplastic resin with no crystallinity, and reinforced fibers exemplified by carbon fibers are included in addition to crystalline thermoplastic resin, it is difficult to acquire an infrared absorption spectrum in which the wavenumber region is from 4,500 cm$^{-1}$ to 2,000 cm$^{-1}$ with sufficient accuracy that can calculate the crystallinity.

As a method for measuring the crystallinity, a thermal melting method using differential scanning calorimetry (DSC) and an X-ray method using X-ray diffraction (XRD) are known. However, the thermal melting method is a method for measuring the crystallinity by melting a resin piece and measuring its melting heat, which is not non-destructive inspection. Thus, this method cannot be used for total inspection for quality guarantee and is not appropriate for use in manufacturing sites. The X-ray method needs a facility protecting the entire device against radiation, and is not appropriate for use in manufacturing sites. In other words, the thermal melting method and the X-ray method both have a problem in that it is difficult to easily measure the crystallinity of crystalline thermoplastic resin.

The present invention has been made in view of the above, and it is an object thereof to provide a crystallinity measurement device, a resin-containing material manufacturing device, a crystallinity measurement method, and a resin-containing material manufacturing method capable of calculating crystallinity easily and accurately even when materials other than crystalline thermoplastic resin are included in addition to crystalline thermoplastic resin.

Solution to Problem

In order to solve the above problems and achieve the object, a crystallinity measurement device includes a Raman spectroscopy unit configured to acquire a Raman spectrum of resin-containing material including crystalline thermoplastic resin; and an analysis unit configured to calculate crystallinity of the crystalline thermoplastic resin based on an intensity of a low-wavenumber spectrum that is a spectrum in a region of less than 600 cm$^{-1}$, in the Raman spectrum.

With this configuration, Raman spectroscopy is used to calculate the crystallinity based on the intensity of a low-wavenumber spectrum that is not affected by molecular oscillation caused by the molecular structure of the resin-containing material. Consequently, the crystallinity can be calculated easily and accurately even when materials other than crystalline thermoplastic resin are included in addition to crystalline thermoplastic resin.

In this configuration, the analysis unit preferably calculates the crystallinity of the crystalline thermoplastic resin based on a ratio of intensities of two low-wavenumber spectra. With this configuration, parameters for calculating the crystallinity can be recognized as units without preparing a reference sample, and hence the crystallinity can be calculated more easily and more accurately.

Further, in order to solve the above problems and achieve the object, a resin-containing material manufacturing device includes a material supply unit configured to supply resin-containing material including crystalline thermoplastic resin; a pressing unit provided on a downstream side of the material supply unit and configured to press the resin-containing material supplied from the material supply unit; a heating unit configured to heat the resin-containing material pressed by the pressing unit; the above-mentioned crystallinity measurement device provided on a downstream side of the pressing unit and the heating unit and configured to measure crystallinity of the crystalline thermoplastic resin included in the resin-containing material that has been subjected to pressing and heating treatment by the pressing unit and the heating unit; and a re-heating unit provided on a downstream side of the crystallinity measurement device and configured to perform re-heating treatment on the resin-containing material including the crystalline thermoplastic resin in accordance with the crystallinity measured by the crystallinity measurement device.

With this configuration, the resin-containing material manufacturing device includes the crystallinity measurement device, and hence it should be understood that Raman spectroscopy is used to calculate the crystallinity based on the intensity of a low-wavenumber spectrum that is not affected by molecular oscillation caused by the molecular structure of the resin-containing material. Consequently, the crystallinity can be calculated easily and accurately even when materials other than crystalline thermoplastic resin are included in addition to crystalline thermoplastic resin. The re-heating unit configured to perform re-heating treatment in accordance with the measured crystallinity is provided, and hence resin-containing material including crystalline thermoplastic resin having desired crystallinity can be obtained in a single series of manufacturing steps.

Further, in order to solve the above problems and achieve the object, a resin-containing material manufacturing device includes a pressing unit having a pressing surface to press resin-containing material including crystalline thermoplastic resin; a heating unit configured to heat the resin-containing material pressed by the pressing unit; the above-mentioned crystallinity measurement device configured to measure crystallinity of the crystalline thermoplastic resin included in the resin-containing material that has been subjected to pressing and heating treatment by the pressing unit and the heating unit respectively; and a light guide unit configured to guide light between the crystallinity measurement device and the pressing surface. The light guide unit guides irradiation light supplied from the Raman spectroscopy unit in the crystallinity measurement device, from the crystallinity measurement device toward the pressing surface, and guides Raman scattered light emitted from the crystalline thermoplastic resin included in the resin-containing material in response to the irradiation light, from the pressing surface toward the crystallinity measurement device. The heating unit adjusts heating in accordance with the crystallinity measured by the crystallinity measurement device.

With this configuration, the resin-containing material manufacturing device includes the crystallinity measurement device, and hence it should be understood that Raman spectroscopy is used to calculate the crystallinity based on the intensity of a low-wavenumber spectrum that is not affected by molecular oscillation caused by the molecular structure of the resin-containing material. Consequently, the crystallinity can be calculated easily and accurately even when materials other than crystalline thermoplastic resin are included in addition to crystalline thermoplastic resin. The light guide unit is provided, and hence Raman spectroscopy treatment by the Raman spectroscopy unit can be performed on resin-containing material that is being subjected to pressing and heating treatment by the pressing unit and the heating unit respectively, as exemplified by a pressing and heating head through the light guide unit. Consequently, the crystallinity can be calculated in real time during the pressing. Thus, the heating can be adjusted in accordance with the measured crystallinity during the pressing and heating treatment, and hence resin-containing material including crystalline thermoplastic resin having desired crystallinity can be obtained in a single series of manufacturing steps.

Further, in order to solve the above problems and achieve the object, a resin-containing material manufacturing device includes a sealed pressing and heating device configured to heat resin-containing material including crystalline thermoplastic resin while pressing the resin-containing material in a sealed state; the above-mentioned crystallinity measurement device configured to measure crystallinity of the crystalline thermoplastic resin included in the resin-containing material that has been subjected to sealed pressing and heating treatment by the sealed pressing and heating device; and a light guide unit configured to guide light between the crystallinity measurement device and inside of the sealed pressing and heating device. The light guide unit guides irradiation light supplied from the Raman spectroscopy unit in the crystallinity measurement device, from the crystallinity measurement device toward the inside of the sealed pressing and heating device, and guides Raman scattered light emitted from the crystalline thermoplastic resin included in the resin-containing material in response to the irradiation light, from the inside of the sealed pressing and heating device toward the crystallinity measurement device. The sealed pressing and heating device adjusts heating in accordance with the crystallinity measured by the crystallinity measurement device.

With this configuration, the resin-containing material manufacturing device includes the crystallinity measurement device, and hence it should be understood that Raman spectroscopy is used to calculate the crystallinity based on the intensity of a low-wavenumber spectrum that is not affected by molecular oscillation caused by the molecular structure of the resin-containing material. Consequently, the crystallinity can be calculated easily and accurately even when materials other than crystalline thermoplastic resin are included in addition to crystalline thermoplastic resin. The light guide unit is provided, and hence Raman spectroscopy treatment by the Raman spectroscopy unit can be performed on resin-containing material that is being subjected to pressing and heating treatment in a sealed state by the sealed pressing and heating device as exemplified by an autoclave device through the light guide unit. Consequently, the crystallinity can be calculated in real time during the pressing. Thus, the heating can be adjusted in accordance with the measured crystallinity during the pressing and heating treatment in the sealed state, and hence resin-containing material including crystalline thermoplastic resin having desired crystallinity can be obtained in a single series of manufacturing steps.

Further, in order to solve the above problems and achieve the object, a crystallinity measurement method includes a Raman spectroscopy step of acquiring a Raman spectrum of resin-containing material including crystalline thermoplastic resin; and a crystallinity calculation step of calculating crystallinity of the crystalline thermoplastic resin based on an intensity of a low-wavenumber spectrum that is a spectrum in a region of less than 600 cm$^{-1}$, in the Raman spectrum acquired at the Raman spectroscopy step. With this configuration, similarly to the above-mentioned corresponding crystallinity measurement device, Raman spectroscopy is used to calculate the crystallinity based on the intensity of a low-wavenumber spectrum that is not affected by molecular oscillation caused by the molecular structure of the resin-containing material. Consequently, the crystallinity can be calculated easily and accurately even when materials other than crystalline thermoplastic resin are included in addition to crystalline thermoplastic resin.

In this configuration, the crystallinity calculation step preferably includes calculating the crystallinity of the crystalline thermoplastic resin based on a ratio of intensities of two low-wavenumber spectra. With this configuration, similarly to the above-mentioned corresponding crystallinity measurement device, parameters for calculating the crystallinity can be recognized as units without preparing a reference sample, and hence the crystallinity can be calculated more easily and more accurately.

Further, in order to solve the above problems and achieve the object, a resin-containing material manufacturing method includes a material supply step of supplying resin-containing material including crystalline thermoplastic resin; a pressing and heating step of heating the resin-containing material supplied at the material supply step while pressing the resin-containing material; a crystallinity measurement step of measuring crystallinity of the crystalline thermoplastic resin included in the resin-containing material that has been subjected to pressing and heating treatment at the pressing and heating step based on the above-mentioned crystallinity measurement method; a re-heating treatment determination step of determining, based on the crystallinity measured at the crystallinity measurement step, whether to perform re-heating treatment on the resin-containing material including the crystalline thermoplastic resin; and a re-heating step of performing, when it is determined at the re-heating treatment determination step to perform the re-heating treatment, the re-heating treatment on the resin-containing material including the crystalline thermoplastic resin. With this configuration, similarly to the above-mentioned corresponding resin-containing material manufacturing device, the resin-containing material manufacturing method includes the above-mentioned crystallinity measurement method, and hence it should be understood that Raman spectroscopy is used to calculate the crystallinity based on the intensity of a low-wavenumber spectrum that is not affected by molecular oscillation caused by the molecular structure of the resin-containing material. Consequently, the crystallinity can be calculated easily and accurately even when materials other than crystalline thermoplastic resin are included in addition to crystalline thermoplastic resin. Re-heating treatment is performed in accordance with the measured crystallinity, and hence resin-containing material including crystalline thermoplastic resin having desired crystallinity can be obtained in a single series of manufacturing steps.

Further, in order to solve the above problems and achieve the object, a resin-containing material manufacturing method includes a pressing and heating start step of starting pressing and heating treatment to heat resin-containing material including crystalline thermoplastic resin while pressing the resin-containing material; a crystallinity measurement step of measuring crystallinity of the crystalline thermoplastic resin included in the resin-containing material that has been subjected to the pressing and heating treatment through the pressing and heating start step based on the above-mentioned crystallinity measurement method; and a pressing and heating adjustment step of adjusting the pressing and heating treatment based on the crystallinity measured at the crystallinity measurement step. With this configuration, similarly to the above-mentioned corresponding resin-containing material manufacturing device, the resin-containing material manufacturing method includes the above-mentioned crystallinity measurement method, and hence it should be understood that Raman spectroscopy is used to calculate the crystallinity based on the intensity of a low-wavenumber spectrum that is not affected by molecular oscillation caused by the molecular structure of the resin-containing material. Consequently, the crystallinity can be calculated easily and accurately even when materials other than crystalline thermoplastic resin are included in addition to the crystalline thermoplastic resin. Raman spectroscopy treatment is performed on the resin-containing material that is being subjected to pressing and heating treatment to calculate the crystallinity in real time during the pressing, and the heating is adjusted in accordance with the measured crystallinity during the pressing and heating treatment. Consequently, resin-containing material including crystalline thermoplastic resin having desired crystallinity can be obtained in a single series of manufacturing steps.

BRIEF DESCRIPTION OF DRAWINGS

FIG. 5 is a flowchart of a resin-containing material manufacturing method including a crystallinity measurement method according to the second embodiment of the present invention.

FIG. 6 is a diagram illustrating a resin-containing material manufacturing device including a crystallinity measurement device according to a third embodiment of the present invention.

DESCRIPTION OF EMBODIMENTS

Embodiments of the present invention are described in detail below with reference to the drawings. Note that the present invention is not limited by the embodiments. Components in the embodiment include the ones that can be easily replaced by a person skilled in the art or include the ones that are substantially the same. The components described below can be combined as appropriate.

First Embodiment

Figure 1:
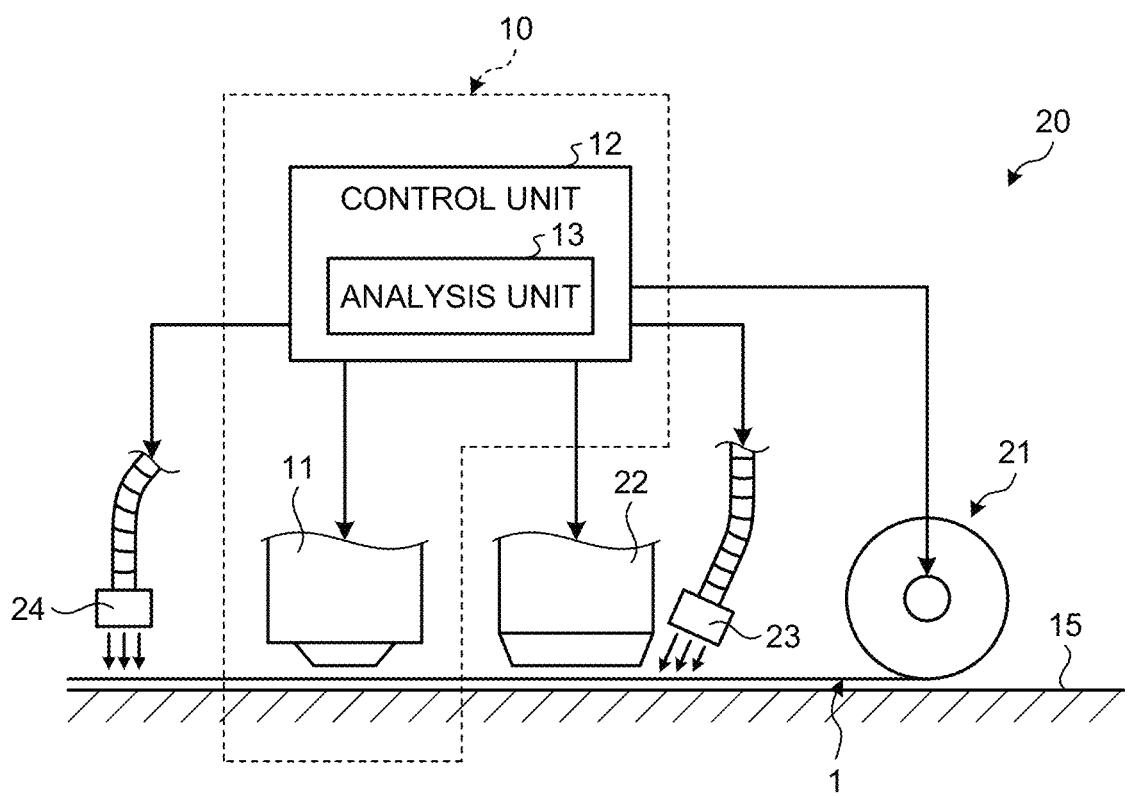
FIG. 1 is a diagram illustrating a resin-containing material manufacturing device including a crystallinity measurement device according to a first embodiment of the present invention.

FIG. 1 is a diagram illustrating a resin-containing material manufacturing device 20 including a crystallinity measurement device 10 according to a first embodiment of the present invention. The crystallinity measurement device 10 illustrated in FIG. 1 measures the crystallinity of resin-containing material 1 including crystalline thermoplastic resin transported on a horizontal table 15. The resin-containing material manufacturing device 20 illustrated in FIG. 1 is a device configured to manufacture the resin-containing material 1, and during the manufacturing of the resin-containing material 1, uses the crystallinity measurement device 10 to measure the crystallinity of crystalline thermoplastic resin included in the resin-containing material 1. The crystallinity of crystalline thermoplastic resin as used herein refers to the proportion of the uncrystallized mass in the crystalline thermoplastic resin to the total of the crystallized mass and the uncrystallized mass, and is expressed in percentage, for example.

The resin-containing material 1 includes crystalline thermoplastic resin. The crystalline thermoplastic resin is resin with crystallinity and thermoplastic property. Polyamide resin, polypropylene resin, polyetheretherketone (PEEK), polyetherketoneketone (PEKK), and polyphenylenesulfide (PPS) are exemplified. The resin-containing material 1 may include materials other than crystalline thermoplastic resin.

Examples of materials other than crystalline thermoplastic resin that may be included in the resin-containing material 1 include amorphous thermoplastic resin, thermosetting resin, and reinforced fibers.

Examples of amorphous thermoplastic resin that may be included in the resin-containing material 1 include acrylonitrile butadiene styrene (ABS) resin. Examples of thermosetting resin that may be included in the resin-containing material 1 include epoxy-based resin, polyester resin, and vinylester resin. Examples of reinforced fibers that may be included in the resin-containing material 1 include carbon fibers, metallic fibers, glass fibers, and plastic fibers obtained by binding several hundreds to several tens of thousands of elementary fibers in the range of from 5 μm or more and 7 μm or less. When the resin-containing material 1 includes reinforced fibers, the resin-containing material 1 becomes fiber-reinforced composite material. When the resin-containing material 1 is composite material, the resin-containing material 1 may be obtained by impregnating reinforced fibers with resin including crystalline thermoplastic resin, or may be commingled material, which is a mixture of reinforced fibers and resin fibers including crystalline thermoplastic resin. When the resin-containing material 1 is commingled material, the resin-containing material 1 includes commingled knit material obtained by weaving reinforced fibers and resin fibers including crystalline thermoplastic resin into a knit pattern.

As illustrated in FIG. 1, the crystallinity measurement device 10 includes a Raman spectroscopy unit 11 and a control unit 12. The Raman spectroscopy unit 11 acquires the Raman spectrum of the resin-containing material 1 including crystalline thermoplastic resin, and is provided to be opposed to a transportation path of the resin-containing material 1 on the horizontal table 15. Specifically, the Raman spectroscopy unit 11 is configured by an excitation light source, a sample irradiation unit, a spectrometer, and a scattered light detector (not shown). The cross-sectional area of Raman scattered light is small and its scattered light is relatively weak, and hence a laser for generating excitation light having a predetermined single wavelength is preferably used as the excitation light source in the Raman spectroscopy unit 11. The sample irradiation unit in the Raman spectroscopy unit 11 is an optical system configured to emit excitation light generated by the excitation light source to the outer side of the Raman spectroscopy unit 11 as irradiation light. The spectrometer in the Raman spectroscopy unit 11 disperses Raman scattered light emitted from the crystalline thermoplastic resin included in the resin-containing material 1 in response to the irradiation light to acquire the Raman spectrum. A polychromator incorporated with diffraction gratings is preferably used. The detector in the Raman spectroscopy unit 11 detects the Raman spectrum obtained by dispersing the Raman scattered light by the spectrometer, and acquires the Raman spectrum as electron information. A photomultiplier tube or a charge coupled device (CCD) detector is preferably used.

The control unit 12 collectively controls the units in the Raman spectroscopy unit 11 and units in the resin-containing material manufacturing device 20 described later, such as a material supply unit 21, a pressing unit 22, a heating unit 23, and a re-heating unit 24. The control unit 12 further includes an analysis unit 13 configured to calculate the crystallinity of crystalline thermoplastic resin based on the intensity of a low-wavenumber spectrum being a spectrum in a region of less than 600 cm$^{-1}$, in the Raman spectrum acquired by the Raman spectroscopy unit 11 as electron information.

The control unit 12 includes an input unit, a storage unit, and a processing unit. Examples of the control unit 12 include a computer. The input unit is, for example, a touch panel integrated with interfaces configured to receive input of various kinds of data from external connected devices and interfaces configured to receive input from users, such as a mouse, a keyboard, and a display device, and transmits the received input information to the storage unit or the processing unit. For example, the storage unit has a storage medium or a storage device such as a random access memory (RAM), a read only memory (ROM), and a flash memory, and stores therein a crystallinity measurement program and a resin-containing material manufacturing program as software programs processed by the processing unit and data referenced by the software programs. The storage unit also functions as a storage area in which the processing unit temporarily stores processing results. The processing unit reads and processes the software programs from the storage unit to implement the functions corresponding to the contents of the software program, specifically, the functions for implementing a crystallinity measurement method according to the embodiments of the present invention by the crystallinity measurement device 10 according to the embodiments of the present invention and the functions for implementing a resin-containing material manufacturing method according to the embodiments of the present invention by the resin-containing material manufacturing device 20 according to the embodiments of the present invention. The processing unit can display information read from the storage unit and processed information on a display device connected to the control unit 12.

Functions of the analysis unit 13 are implemented when an arithmetic processing unit executes a crystallinity measurement program stored in a ROM onto a RAM. Note that the functions of the analysis unit 13 are described in detail later in the description of a crystallinity measurement method.

As illustrated in FIG. 1, the resin-containing material manufacturing device 20 includes the crystallinity measurement device 10, the material supply unit 21, the pressing unit 22, the heating unit 23, and the re-heating unit 24. The material supply unit 21 supplies plate-shaped resin-containing material 1 formed to extend in a transportation direction to the downstream side of the transportation path while rewinding the resin-containing material 1 wound into a roll.

The pressing unit 22 is provided on the downstream side of the material supply unit 21 so as to be opposed to the horizontal table 15 in the transportation path of the resin-containing material 1 on the horizontal table 15, and presses the resin-containing material 1 supplied from the material supply unit 21. Examples of the pressing unit 22 include a pressing head configured to press the resin-containing material 1 located between the horizontal table 15 and the pressing unit 22 along the vertical direction by pressing a pressing surface thereof extending along the horizontal direction against the horizontal table 15.

The heating unit 23 is provided near the pressing unit 22 so as to be opposed to the horizontal table 15, and heats the resin-containing material 1 that is being pressed by the pressing unit 22. Note that, in the first embodiment, the heating unit 23 is provided near the pressing unit 22, but the present invention is not limited thereto, and the heating unit 23 may be provided so as to be incorporated in the pressing unit 22.

The heating unit 23 may be of any well-known heating type. A heating type that directly affects heating action on the resin-containing material 1 through the pressing unit 22 or the horizontal table 15 is preferred. Specific examples of the heating unit 23 include an infrared heating type. When the resin-containing material 1 includes reinforced fibers having electric conductivity as exemplified by carbon fibers and metallic fibers, it is preferred that the heating unit 23 use an induction magnetic heating type and an induction electric heating type.

In the case where the heating unit 23 is provided to be incorporated in the pressing unit 22, iron powder that generates heat when applied with magnetic field or a heat generating element as exemplified by an electromagnetic field heat generating element such as metal is provided on the pressing surface side of the pressing unit 22, and a method for heating the resin-containing material 1 through the heat generating element may be used. When the electromagnetic field heat generating element such as metal is applied with electric field along a predetermined direction in the electromagnetic field heat generating element such as metal, molecular momentum increases, and heat generation inside the electromagnetic field heat generating element such as metal is induced. When the electromagnetic field heat generating element such as metal is applied with magnetic field along a direction orthogonal to the predetermined direction in the electromagnetic field heat generating element such as metal, current is generated inside and heat is generated due to electric resistance of the electromagnetic field heat generating element such as metal itself. Similarly, the electromagnetic field heat generating element such as metal absorbs electromagnetic waves to generate heat. For example, the electromagnetic field heat generating element such as metal is provided as a sheet of the electromagnetic field heat generating element such as metal that is coated by being dispersed in a solution and sprayed.

In the resin-containing material manufacturing device 20, the crystallinity measurement device 10 is provided on the downstream side of the pressing unit 22 and the heating unit 23 in the transportation path of the resin-containing material 1 on the horizontal table 15, and measures the crystallinity of crystalline thermoplastic resin included in the resin-containing material 1 that has been subjected to pressing and heating treatment by the pressing unit 22 and the heating unit 23 respectively.

The re-heating unit 24 is provided on the downstream side of the crystallinity measurement device 10 in the transportation path of the resin-containing material 1 on the horizontal table 15, and preforms re-heating treatment on the resin-containing material 1 including the crystalline thermoplastic resin in accordance with the crystallinity measured by the crystallinity measurement device 10. Specifically, the same heating type as the heating unit 23 is preferably used for the re-heating unit 24.

Figure 2:
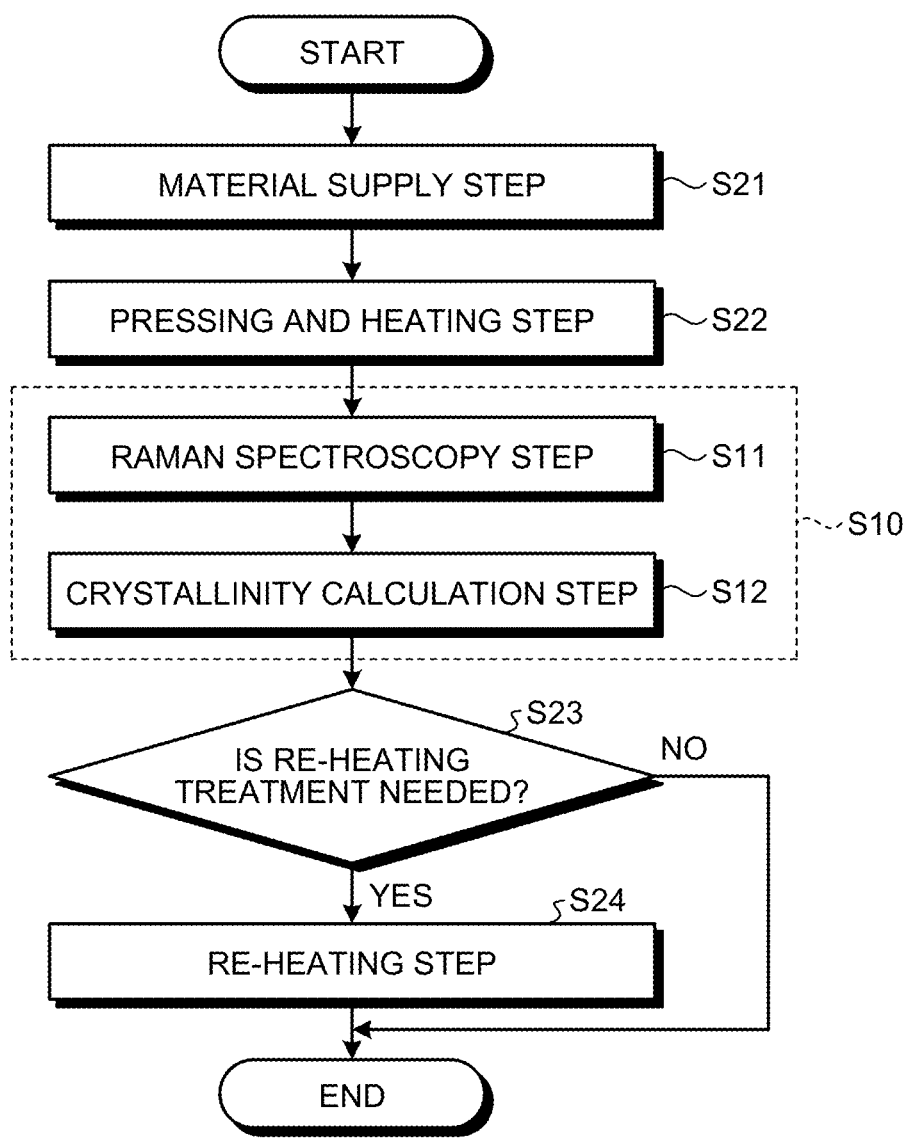
FIG. 2 is a flowchart of a resin-containing material manufacturing method including a crystallinity measurement method according to the first embodiment of the present invention.

FIG. 2 is a flowchart of a resin-containing material manufacturing method including a crystallinity measurement method according to the first embodiment of the present invention. The crystallinity measurement method and the resin-containing material manufacturing method according to the first embodiment are described with reference to FIG. 2. The crystallinity measurement method according to the first embodiment is executed by the crystallinity measurement device 10, and the resin-containing material manufacturing method according to the first embodiment is executed by the resin-containing material manufacturing device 20. As illustrated in FIG. 2, the crystallinity measurement method according to the first embodiment includes a Raman spectroscopy step S11 and a crystallinity calculation step S12. As illustrated in FIG. 2, the resin-containing material manufacturing method according to the first embodiment includes a material supply step S21, a pressing and heating step S22, a crystallinity measurement step S10 including a Raman spectroscopy step S11 and a crystallinity calculation step S12, a re-heating treatment determination step S23, and a re-heating step S24.

The material supply step S21 is a step in which the material supply unit 21 supplies resin-containing material 1 including crystalline thermoplastic resin to a transportation path of the resin-containing material 1 on the horizontal table 15. The pressing and heating step S22 is a step in which the heating unit 23 heats the resin-containing material 1 supplied at the material supply step S21 while the pressing unit 22 presses the resin-containing material 1. In this manner, the resin-containing material 1 is subjected to pressing and heating treatment, and various kinds of gases contained therein are removed such that the resin-containing material 1 is formed into a desired shape.

At the crystallinity measurement step S10, the crystallinity of the crystalline thermoplastic resin included in the resin-containing material 1 that has been subjected to the pressing and heating treatment at the pressing and heating step S22 is measured. In the crystallinity measurement step S10, the Raman spectroscopy step S11 is a step of acquiring the Raman spectrum of the resin-containing material 1 including the crystalline thermoplastic resin. Specifically, at the Raman spectroscopy step S11, in the crystallinity measurement device 10, the excitation light source generates excitation light for the crystalline thermoplastic resin, the sample irradiation unit irradiates the resin-containing material 1 with the excitation light, the spectrometer disperses Raman scattered light emitted from the crystalline thermoplastic resin included in the resin-containing material 1 in response to the irradiation light to acquire the Raman spectrum, and the detector detects and acquires the Raman spectrum as electron information.

The crystallinity calculation step S12 is a step of calculating the crystallinity of the crystalline thermoplastic resin included in the resin-containing material 1 based on the intensity of a low-wavenumber spectrum being a spectrum in a region of less than 600 cm$^{-1}$, in the Raman spectrum acquired at the Raman spectroscopy step S11.

Figure 3:
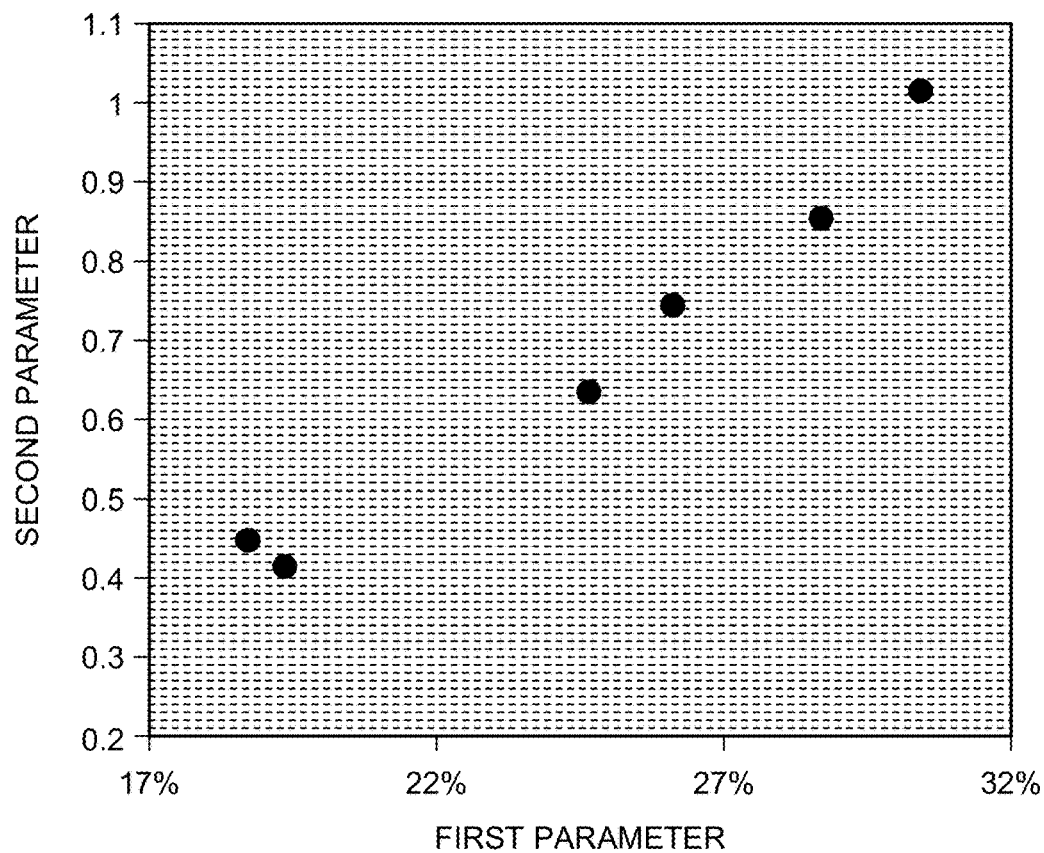
FIG. 3 is a graph for describing parameters used in the crystallinity measurement method in FIG. 2.

FIG. 3 is a graph for describing parameters used in the crystallinity measurement method in FIG. 2. In the graph illustrated in FIG. 3, the horizontal axis is a first parameter, and the vertical axis is a second parameter. The first parameter in the graph illustrated in FIG. 3 is crystallinity of a sample of predetermined crystalline thermoplastic resin measured by using X-ray diffraction. The second parameter in the graph illustrated in FIG. 3 is a ratio of the intensity of a spectrum of 34 cm$^{-1}$ in the Raman spectrum acquired by using excitation light of 1,064 nm to the intensity of a spectrum of 97 cm$^{-1}$ for the same sample of predetermined crystalline thermoplastic resin as the sample whose crystallinity has been measured by using X-ray diffraction. The first parameter and the second parameter have a linear relation as illustrated in FIG. 3, and hence it is understood that the second parameter is used to easily measure the crystallinity of crystalline thermoplastic resin by using Raman spectroscopy with the same accuracy as in the case of using X-ray diffraction.

At the crystallinity calculation step S12, the analysis unit 13 acquires and uses the correlation between the first parameter and the second parameter stored in the storage unit in the control unit 12 to calculate the crystallinity of the crystalline thermoplastic resin based on the intensity of a low-wavenumber spectrum being a spectrum in a region of less than 600 cm$^{-1}$, in the Raman spectrum acquired by the Raman spectroscopy unit 11 as electron information at the Raman spectroscopy step S11. At the crystallinity calculation step S12, it is preferred that the analysis unit 13 calculate the crystallinity of the crystalline thermoplastic resin based on the ratio of intensities of two low frequency spectra as described above with reference to FIG. 3.

The re-heating treatment determination step S23 is a step in which the control unit 12 determines, based on the crystallinity of the crystalline thermoplastic resin measured at the crystallinity measurement step S10, whether to perform re-heating treatment on the resin-containing material 1 including the crystalline thermoplastic resin. Specifically, at the re-heating treatment determination step S23, when the crystallinity of the crystalline thermoplastic resin measured at the crystallinity measurement step S10 is within a desired range, the control unit 12 determines that the quality of various physical parameters depending on the crystallinity are sufficiently guaranteed, and determines that it is not necessary to perform re-heating treatment on the resin-containing material 1 including the crystalline thermoplastic resin, and the flow proceeds to No in the flowchart in FIG. 2. At the re-heating treatment determination step S23, on the other hand, when the crystallinity of the crystalline thermoplastic resin measured at the crystallinity measurement step S10 is outside the desired range, the control unit 12 determines that there is a room for improvement on the quality of various physical parameters depending on the crystallinity, and determines that it is necessary to perform re-heating treatment on the resin-containing material 1 including the crystalline thermoplastic resin, and the flow proceeds to Yes in the flowchart in FIG. 2.

At the re-heating step S24, when it is determined at the re-heating treatment determination step S23 to preform re-heating treatment (Yes at re-heating treatment determination step S23), re-heating treatment is performed on the resin-containing material 1 including the crystalline thermoplastic resin. At the re-heating step S24, when it is determined at the re-heating treatment determination step S23 not to perform re-heating treatment (No at re-heating treatment determination step S23), this step is not executed.

In this manner, when the resin-containing material 1 including crystalline thermoplastic resin having desired crystallinity is obtained at the pressing and heating step S22, the re-heating step S24 is not executed, and the resin-containing material 1 including the crystalline thermoplastic resin having desired crystallinity can be directly obtained. When the resin-containing material 1 including crystalline thermoplastic resin having desired crystallinity is not obtained at the pressing and heating step S22, the re-heating step S24 is executed to re-adjust the crystallinity, and the resin-containing material 1 including crystalline thermoplastic resin having desired crystallinity can be obtained.

The crystallinity measurement device 10 and the crystallinity measurement method according to the first embodiment have the configurations as described above, and hence Raman spectroscopy is used to calculate the crystallinity based on the intensity of a low-wavenumber spectrum that is not affected by molecular oscillation caused by the molecular structure of the resin-containing material 1. Consequently, the crystallinity can be calculated easily and accurately even when materials other than crystalline thermoplastic resin are included in addition to crystalline thermoplastic resin. The crystallinity measurement device 10 and the crystallinity measurement method according to the first embodiment eliminate the need of performing destructive inspection by thermal melting and the need of providing a radioprotective facility for an X-ray method unlike the conventional cases. The crystallinity measurement device 10 and the crystallinity measurement method according to the first embodiment are inventions that have been made as a result of diligent study by the inventors of the present invention by focusing on a spectrum in a region of less than 600 cm$^{-1}$, which is naturally ignored because it is a region from which information on molecular oscillation caused by molecular structure cannot be acquired by conventional general Raman spectroscopy, preferably spectra in a region of 100 cm$^{-1}$ or more and 200 cm$^{-1}$ or less, and finding for the first time the fact that the crystallinity of crystalline thermoplastic resin can be easily measured by using the spectrum in the region, thereby exhibiting various effects.

In the crystallinity measurement device 10 and the crystallinity measurement method according to the first embodiment, the analysis unit 13 calculates the crystallinity of crystalline thermoplastic resin based on the ratio of intensities of two low-wavenumber spectra. Thus, in the crystallinity measurement device 10 and the crystallinity measurement method according to the first embodiment, no reference sample needs to be prepared as in Patent Literature 1, but the parameters for calculating the crystallinity can be recognized as units. Consequently, the crystallinity can be calculated more easily and more accurately.

The resin-containing material manufacturing device 20 and the resin-containing material manufacturing method according to the first embodiment include the crystallinity measurement device 10 and the crystallinity measurement method according to the first embodiment, respectively, and hence it should be understood that Raman spectroscopy is used to calculate the crystallinity based on the intensity of a low-wavenumber spectrum that is not affected by molecular oscillation caused by the molecular structure of the resin-containing material 1. Consequently, the crystallinity can be calculated easily and accurately even when materials other than crystalline thermoplastic resin are included in addition to crystalline thermoplastic resin. The resin-containing material manufacturing device 20 and the resin-containing material manufacturing method according to the first embodiment include the re-heating unit 24 configured to perform re-heating treatment in accordance with the measured crystallinity, and hence resin-containing material 1 including crystalline thermoplastic resin having desired crystallinity can be obtained in a single series of manufacturing steps.

Second Embodiment

Figure 4:
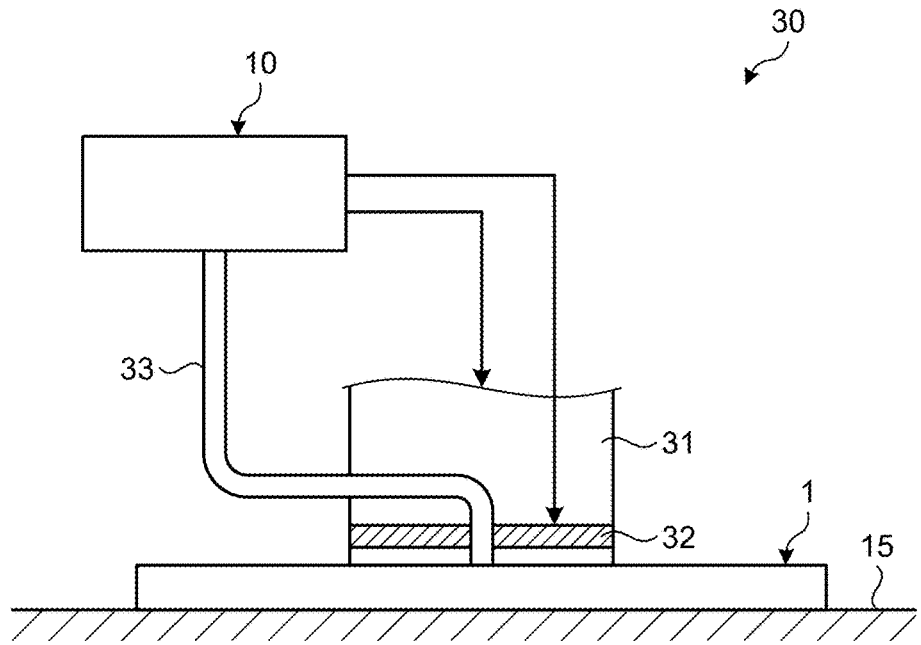
FIG. 4 is a diagram illustrating a resin-containing material manufacturing device including a crystallinity measurement device according to a second embodiment of the present invention.

FIG. 4 is a diagram illustrating a resin-containing material manufacturing device 30 including a crystallinity measurement device 10 according to a second embodiment of the present invention. The resin-containing material manufacturing device 30 according to the second embodiment includes a crystallinity measurement device 10 similarly to the resin-containing material manufacturing device 20 according to the first embodiment. In the resin-containing material manufacturing device 30 according to the second embodiment, the same configurations as in the resin-containing material manufacturing device 20 according to the first embodiment are denoted by the same reference symbols as in the first embodiment, and detailed descriptions thereof are omitted.

As illustrated in FIG. 4, the resin-containing material manufacturing device 30 includes a pressing unit 31, a heating unit 32, the crystallinity measurement device 10, and a light guide unit 33. The pressing unit 31 is the same as the pressing unit 22 except that the heating unit 32 is incorporated and the light guide unit 33 is provided to pass through the inside of the pressing unit 31. The heating unit 32 is the same as the heating unit 23 except that the heating unit 32 is incorporated in the pressing unit 31. In the second embodiment, the pressing unit 31 and the heating unit 32 together constitute a pressing and heating head.

The crystallinity measurement device 10 according to the second embodiment is different from the crystallinity measurement device 10 according to the first embodiment in that the control unit 12 collectively controls the pressing unit 31 and the heating unit 32 as the units in the resin-containing material manufacturing device 30 instead of collectively controlling the material supply unit 21, the pressing unit 22, the heating unit 23, and the re-heating unit 24 as the units in the resin-containing material manufacturing device 20, and are similar in the other configurations.

The light guide unit 33 is provided across the crystallinity measurement device 10 and a pressing surface of the pressing unit 31. The light guide unit 33 is provided so as to guide irradiation light supplied from the Raman spectroscopy unit 11 in the crystallinity measurement device 10, from the crystallinity measurement device 10 toward the pressing surface of the pressing unit 31, and irradiate the resin-containing material 1 facing the pressing surface of the pressing unit 31 with the irradiation light. The light guide unit 33 is provided so as to guide Raman scattered light emitted from the crystalline thermoplastic resin included in the resin-containing material 1 in response to the irradiation light, from the pressing surface of the pressing unit 31 toward the Raman spectroscopy unit 11 in the crystallinity measurement device 10, so that the Raman spectroscopy unit 11 in the crystallinity measurement device 10 can detect the Raman spectrum based on the Raman scattered light through a spectrometer and a detector and acquire the Raman spectrum as electron information. Examples of the light guide unit 33 include an optical fiber that is light guide material capable of guiding irradiation light supplied from the Raman spectroscopy unit 11 in the crystallinity measurement device 10 and Raman scattered light emitted from the crystalline thermoplastic resin included in the resin-containing material 1 in response to the irradiation light.

FIG. 5 is a flowchart of a resin-containing material manufacturing method including a crystallinity measurement method according to the second embodiment of the present invention. The crystallinity measurement method and the resin-containing material manufacturing method according to the second embodiment are described with reference to FIG. 5. The crystallinity measurement method according to the second embodiment is executed by the crystallinity measurement device 10 similarly to the crystallinity measurement method according to the first embodiment, and the resin-containing material manufacturing method according to the second embodiment is executed by the resin-containing material manufacturing device 30. The crystallinity measurement method according to the second embodiment is the same as the crystallinity measurement method according to the first embodiment, and hence detailed descriptions thereof are omitted. As illustrated in FIG. 5, the resin-containing material manufacturing method according to the second embodiment includes a material supply step S31, a pressing and heating start step S32, the same crystallinity measurement step S10 as in the first embodiment, a pressing and heating adjustment step S33, and a pressing and heating finish determination step S34.

The material supply step S31 is a step of supplying resin-containing material 1 including crystalline thermoplastic resin between the horizontal table 15 and the pressing surface of the pressing unit 31. The material supply step S31 may employ the same method as in the material supply step S21 according to the first embodiment, or may employ another supply method.

The pressing and heating start step S32 is a step in which the pressing unit 31 starts to press the resin-containing material 1 supplied at the material supply step S31 and the heating unit 32 starts to heat the resin-containing material 1. In this manner, pressing and heating treatment on the resin-containing material 1 is started. In the second embodiment, at the crystallinity measurement step S10, the analysis unit 13 measures the crystallinity of the crystalline thermoplastic resin included in the resin-containing material 1 that has been subjected to the pressing and heating treatment through the pressing and heating start step S32. At the crystallinity measurement step S10, the Raman spectroscopy unit 11 in the crystallinity measurement device 10 irradiates the resin-containing material 1 with irradiation light through the light guide unit 33, and receives Raman scattered light emitted from the resin-containing material 1 through the light guide unit 33.

The pressing and heating adjustment step S33 is a step in which the control unit 12 adjusts the pressing and heating treatment based on the crystallinity of the crystalline thermoplastic resin included in the resin-containing material 1 measured at the crystallinity measurement step S10. Specifically, at the pressing and heating adjustment step S33, the control unit 12 adjusts heating temperature of the heating unit 32 such that the crystallinity approaches the desired one depending on whether the crystallinity of crystalline thermoplastic resin included in the resin-containing material 1 measured at the crystallinity measurement step S10 is higher or lower than the desired crystallinity or how the crystallinities are different.

The pressing and heating finish determination step S34 is a step in which the control unit 12 determines whether to finish the pressing and heating treatment on the resin-containing material 1. Specifically, at the pressing and heating finish determination step S34, when the control unit 12 determines that the crystallinity of the crystalline thermoplastic resin included in the resin-containing material 1 is within a predetermined region including desired crystallinity, the control unit 12 determines to finish the pressing and heating treatment on the resin-containing material 1, and the flow proceeds to Yes in the flowchart in FIG. 5. At the pressing and heating finish determination step S34, on the other hand, when the control unit 12 determines that the crystallinity of the crystalline thermoplastic resin included in the resin-containing material 1 is outside the predetermined region including desired crystallinity, the control unit 12 determines that it is necessary to re-adjust the crystallinity of the crystalline thermoplastic resin included in the resin-containing material 1, and determines not to finish the pressing and heating treatment on the resin-containing material 1, and the flow proceeds to No in the flowchart in FIG. 5.

The crystallinity measurement step S10 and the pressing and heating adjustment step S33 are repeatedly executed until it is determined at the pressing and heating finish determination step S34 to finish the pressing and heating treatment, that is, until it is determined that the crystallinity of the crystalline thermoplastic resin included in the resin-containing material 1 is within the predetermined region including desired crystallinity. Such treatment is performed, and hence the resin-containing material 1 including crystalline thermoplastic resin having desired crystallinity can be obtained.

The resin-containing material manufacturing device 30 and the resin-containing material manufacturing method according to the second embodiment include the crystallinity measurement device 10 and the crystallinity measurement method according to the second embodiment, respectively, and hence it should be understood that Raman spectroscopy is used to calculate the crystallinity based on the intensity of a low-wavenumber spectrum that is not affected by molecular oscillation caused by the molecular structure of the resin-containing material 1. Consequently, the crystallinity can be calculated easily and accurately even when materials other than crystalline thermoplastic resin are included in addition to crystalline thermoplastic resin. In the resin-containing material manufacturing device 30 and the resin-containing material manufacturing method according to the second embodiment, Raman spectroscopy treatment by the Raman spectroscopy unit 11 can be performed on resin-containing material 1 that is being subjected to pressing and heating treatment by the pressing unit 31 and the heating unit 32 as exemplified by a pressing and heating head through the light guide unit 33. Consequently, the crystallinity can be calculated in real time during the pressing. Accordingly, the resin-containing material manufacturing device 30 and the resin-containing material manufacturing method according to the second embodiment can adjust the heating in accordance with the measured crystallinity during the pressing and heating treatment, and hence can obtain resin-containing material 1 including crystalline thermoplastic resin having desired crystallinity in a single series of manufacturing steps.

Third Embodiment

FIG. 6 is a diagram illustrating a resin-containing material manufacturing device 40 including a crystallinity measurement device 10 according to a third embodiment of the present invention. A resin-containing material manufacturing device 40 according to the third embodiment includes a crystallinity measurement device 10 similarly to the resin-containing material manufacturing device 20 according to the first embodiment and the resin-containing material manufacturing device 30 according to the second embodiment. In the resin-containing material manufacturing device 40 according to the third embodiment, the same configurations as in the resin-containing material manufacturing device 20 according to the first embodiment are denoted by the same reference symbol groups as in the first embodiment and the same configurations as in the resin-containing material manufacturing device 30 according to the second embodiment are denoted by the same reference symbol groups as in the second embodiment, and detailed descriptions thereof are omitted.

As illustrated in FIG. 6, the resin-containing material manufacturing device 40 includes a sealed pressing and heating device 41, a crystallinity measurement device 10, and a light guide unit 33. The sealed pressing and heating device 41 heats resin-containing material 1 including crystalline thermoplastic resin while pressing the resin-containing material 1 in a sealed state. Specific examples thereof include an autoclave device configured to heat resin-containing material 1 under pressing by increasing the pressure inside the device with gas.

The crystallinity measurement device 10 according to the third embodiment is different from the crystallinity measurement device 10 according to the first embodiment in that the control unit 12 collectively controls the sealed pressing and heating device 41 as a unit in the resin-containing material manufacturing device 40 instead of collectively controlling the material supply unit 21, the pressing unit 22, the heating unit 23, and the re-heating unit 24 as the units in the resin-containing material manufacturing device 20, and are similar in the other configurations.

In the third embodiment, the light guide unit 33 is provided across the crystallinity measurement device 10 and a location where the resin-containing material 1 is placed in the sealed pressing and heating device 41. In the third embodiment, the light guide unit 33 is provided so as to guide irradiation light supplied from the Raman spectroscopy unit 11 in the crystallinity measurement device 10 from the crystallinity measurement device 10 toward the surface of the resin-containing material 1 placed inside the sealed pressing and heating device 41, and irradiate the resin-containing material 1 with the irradiation light. In the third embodiment, the light guide unit 33 is provided so as to guide Raman scattered light emitted from the crystalline thermoplastic resin included in the resin-containing material 1 in response to the irradiation light, toward the Raman spectroscopy unit 11 in the crystallinity measurement device 10 provided outside the sealed pressing and heating device 41, so that the Raman spectroscopy unit 11 in the crystallinity measurement device 10 can detect the Raman spectrum based on the Raman scattered light through a spectrometer and a detector and acquire the Raman spectrum as electron information. As the light guide unit 33 according to the third embodiment, the same light guide unit as in the second embodiment is exemplified.

A crystallinity measurement method and a resin-containing material manufacturing method according to the third embodiment are described. The crystallinity measurement method according to the third embodiment is obtained by, in the crystallinity measurement method according to the second embodiment, changing the supply destination of resin-containing material 1 including crystalline thermoplastic resin at the material supply step S31 from the region between the horizontal table 15 and the pressing surface of the pressing unit 31 to a placement position inside the sealed pressing and heating device 41, and changing the subject that executes the pressing and heating start step S32 and the pressing and heating adjustment step S33 from the pressing unit 31 and the heating unit 32 to the sealed pressing and heating device 41. The other configurations are the same.

The resin-containing material manufacturing device 40 and the resin-containing material manufacturing method according to the third embodiment have the configurations as described above, and hence even when the sealed pressing and heating device 41 exemplified by an autoclave device is used, the same functions and effects as those of the resin-containing material manufacturing device 30 and the resin-containing material manufacturing method according to the second embodiment are obtained.

REFERENCE SIGNS LIST

1 Resin-containing material
10 Crystallinity measurement device
11 Raman spectroscopy unit
12 Control unit
13 Analysis unit
15 Horizontal table
20, 30, 40 Resin-containing material manufacturing device
21 Material supply unit
22, 31 Pressing unit
23, 32 Heating unit 24 Re-heating unit
33 Light guide unit
41 Sealed pressing and heating device

The invention claimed is:

1. A crystallinity measurement method, comprising:
acquiring a Raman spectrum of resin-containing material including crystalline thermoplastic resin by irradiating the resin-containing material with excitation light and spectrally dispersing Raman scattered light emitted from the crystalline thermoplastic resin contained in the resin-containing material; and
calculating crystallinity of the crystalline thermoplastic resin based on an intensity of a low-wavenumber spectrum that is a spectrum in a region of less than 600 $cm^{-1}$, in the acquired Raman spectrum, by calculating a ratio of the intensity of two low wavenumber spectrums,
obtaining a correlation information indicating the correlation between the ratio of the intensity and the crystallinity of the crystalline thermoplastic resin, and calculating the crystallinity of the crystalline thermoplastic resin based on the calculated ratio of the intensity and the obtained correlation information.

2. The crystallinity measurement method according to claim 1, wherein:
a Raman spectroscopy unit is used to acquire the Raman spectrum of resin-containing material including crystalline thermoplastic resin; and
an analysis unit is used to calculate the crystallinity of the crystalline thermoplastic resin based on the intensity of the low-wavenumber spectrum that is the spectrum in the region of less than 600 $cm^{-1}$, in the Raman spectrum.

3. The crystallinity measurement method according to claim 2, wherein the analysis unit calculates the crystallinity of the crystalline thermoplastic resin based on a ratio of intensities of two low-wavenumber spectra.

* * * * *